US009042957B2

(12) United States Patent
Li et al.

(10) Patent No.: US 9,042,957 B2
(45) Date of Patent: May 26, 2015

(54) DEVICE AND METHOD FOR ELECTROIMPEDANCE TOMOGRAPHY

(75) Inventors: Jianhua Li, Lübeck (DE); Thomas Gallus, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 411 days.

(21) Appl. No.: 13/365,561

(22) Filed: Feb. 3, 2012

(65) Prior Publication Data

US 2012/0271193 A1    Oct. 25, 2012

(30) Foreign Application Priority Data

Apr. 23, 2011  (DE) .................. 10 2011 018 505

(51) Int. Cl.
*A61B 5/04* (2006.01)
*A61B 5/05* (2006.01)
*A61B 5/053* (2006.01)
*A61B 5/00* (2006.01)

(52) U.S. Cl.
CPC ............. *A61B 5/0536* (2013.01); *A61B 5/6801* (2013.01); *A61B 5/6831* (2013.01); *A61B 2562/227* (2013.01)

(58) Field of Classification Search
CPC ............ A61B 5/05; A61B 5/053; A61B 5/04; A61B 5/0536; A61B 5/6801; A61B 5/6831; A61B 2562/227
USPC .......... 600/547, 506, 324, 536, 382, 390, 393
See application file for complete search history.

(56) References Cited

U.S. PATENT DOCUMENTS

| 4,391,279 | A  | * | 7/1983  | Stein .............................. 600/387 |
| 5,720,296 | A  | * | 2/1998  | Cha ................................ 600/554 |
| 5,919,142 | A  |   | 7/1999  | Boone et al. |
| 5,987,353 | A  | * | 11/1999 | Khatchatrian et al. ........ 600/547 |
| 6,760,629 | B2 | * | 7/2004  | Minogue et al. .............. 607/149 |
| 7,162,296 | B2 | * | 1/2007  | Leonhardt et al. ............ 600/547 |
| 7,315,754 | B2 | * | 1/2008  | Leonhardt et al. ............ 600/390 |
| 2005/0107719 | A1 |   | 5/2005  | Arad |
| 2006/0058600 | A1 | * | 3/2006  | Eichler ......................... 600/407 |
| 2006/0084855 | A1 | * | 4/2006  | Teschner et al. .............. 600/390 |
| 2007/0010758 | A1 | * | 1/2007  | Matthiessen et al. ......... 600/547 |
| 2009/0105574 | A1 | * | 4/2009  | Young ........................... 600/372 |
| 2010/0049027 | A1 | * | 2/2010  | Teschner et al. .............. 600/390 |
| 2010/0049077 | A1 | * | 2/2010  | Sadleir et al. ................. 600/547 |

FOREIGN PATENT DOCUMENTS

| DE | 695 05 799 T2 | 4/1999 |
| DE | 101 56 833 A1 | 5/2003 |
| DE | 103 15 863 A1 | 10/2004 |
| EP | 1 649 805 B1  | 11/2009 |

* cited by examiner

*Primary Examiner* — Devin Henson
(74) *Attorney, Agent, or Firm* — McGlew and Tuttle, P.C.

(57) ABSTRACT

A device for electroimpedance tomography with an electrode belt (2), which has electrodes (E1 . . . E16), wherein at least two groups (5, 6) of electrodes located next to each other are formed and the electrodes of one group are contacted with at least one, multiwire feed cable (7, 8). For a reduced noise level during data acquisition, provisions are made for at least one electrode (E9) of two mutually adjacently located electrodes (E8, E9) of two different groups (5, 6) to have an additional electrode feed line (15), which is led over the feed cable (7) of the adjacent group (5).

8 Claims, 3 Drawing Sheets

DEVICE AND METHOD FOR ELECTROIMPEDANCE TOMOGRAPHY

CROSS REFERENCE TO RELATED APPLICATIONS

This application claims the benefit of priority under 35 U.S.C. §119 of German Patent Application DE 10 2011 018 505.4 filed Apr. 23, 2011, the entire contents of which are incorporated herein by reference.

FIELD OF THE INVENTION

The present invention pertains to a device for electroimpedance tomography and to a method for determining measured signals with a device for electroimpedance tomography.

BACKGROUND OF THE INVENTION

Electroimpedance tomography (EIT) is increasingly used in medicine. Typical EIT devices use 8, 16 or 32 electrodes for data acquisition, current being fed through two electrodes and the resulting voltage being measured between the remaining electrodes. By combining different feeds and measurements, it is possible to generate a signal vector, from which the impedance distribution can be determined by means of a suitable algorithm or the relative change in the impedance distribution relative to a reference value can be determined in the electrode plane in functional EIT (fEIT). The latter method is used in status-dependent functional electroimpedance of the thorax, in which N electrodes are arranged around the thorax in a ring-shaped pattern in order to reconstruct a tomogram of the ventilation-related relative impedance change, which is an indicator of the regional distribution of the ventilation of the lungs, from the comparison of the signal vectors in different states of the lungs, e.g., end-inspiratory and end-expiratory states. Thoracic fEIT is well suited for the regionally resolved lung monitoring of ventilation, especially in intensive care units in hospitals.

A device for electroimpedance tomography is disclosed, for example, in U.S. Pat. No. 5,919,142 A.

The so-called adjacent data acquisition, in which current is fed through two adjacent electrodes and the voltages between the remaining electrodes are measured adjacent to each other, wherein current-carrying electrodes are left out because of the unknown voltage drop over the current-carrying electrodes, is a frequently used data acquisition strategy. Thus, thirteen voltage values are obtained for a current feed position. Thirteen voltages are again obtained for the current feed via a subsequent electrode pair, so that a total of 16*13=208 voltage measured values are present, from which the impedance distribution or relative change in impedance distribution can be determined with the use of 208 reference voltages with a reconstruction rule, which is applicable to this form of data acquisition.

Electrode belts, which consist of a support structure, to which the electrodes are attached and held in position, are usually used to attach the electrodes to the body of a test subject. Such an electrode belt is known from the document EP 1 649 805 B1, which forms this class. The electrodes are in flat contact with the body of the test subject and have a contact means, to which an electrode feed line each is connected as a lead of a multiwire feed cable. The effect of interferences is reduced by shielding each electrode feed line.

The electrode belt is divided into two groups of eight electrodes each, which are contacted each to a separate, multiwire feed cable. The multiwire feed cable has two strands, with which four electrodes are contacted.

Magnetic fields, which compromise the voltage measurements, may develop due to the current feed at adjacent electrodes. This magnetic cross-talk is slight as long as the electrode feed lines affected extend within a single multiwire feed cable. If a multiwire feed cable is located on the right-hand side and left-hand side of the electrode belt, the magnetic cross-talk is slight as long as the electrode feed lines for the current feed and the voltage measurement extend exclusively in the right-hand or left-hand feed cable. The maximum cross-talk occurs if the electrode feed lines for the electrode pairs for current feed and voltage measurement electrode pairs extend in different feed cables.

SUMMARY OF THE INVENTION

A basic object of the present invention is to improve a device of the above-mentioned type concerning the noise level during data acquisition at the electrode belt and to propose a method for determining measured values with a device for electroimpedance tomography.

According to the invention a device is provided for electroimpedance tomography. The device comprises an electrode belt with electrodes comprising a first group of electrodes and a second group of electrodes. The first group of electrodes is located adjacent to the second group of electrodes. The electrodes include an adjacent pair of electrodes comprising an electrode of the first group of electrodes located adjacent to an electrode of the second group of electrodes. A first group multiwire feed cable is provided comprising electrode feed lines electrically connected to respective electrodes of the first group of electrodes and a second group multiwire feed cable is provided comprising electrode feed lines electrically connected to respective electrodes of the second group of electrodes. At least one of the adjacent electrodes has an additional electrode feed line, which is led over the feed cable of the adjacent group.

The device may advantageously include a belt buckle at the electrode belt, wherein the two groups of electrodes are located on each of two sides of the belt buckle. The electrodes located adjacent to each other that are from different groups may be located at the beginning of the belt on both sides of the belt buckle or at the end of the respective group.

According to a further aspect of the invention, a method is provided for determining measured signals with a device for electroimpedance tomography. The method comprises the steps of providing an electrode belt comprising at least two groups of electrodes located next to each other, which are contacted each via multiwire feed cables and electrically connecting at least one electrode of two adjacent electrodes which belong to different groups, with an additional electrode feed line, which extends via the feed cable of adjacent group of electrodes.

In a device for electroimpedance tomography with an electrode belt, which has electrodes, groups of electrodes located next to each other are formed. Electrodes that belong to one group are contacted with at least one multiwire feed cable. The groups may have an equal number of electrodes or different numbers of electrodes. Provisions are made according to the present invention for at least one electrode of two electrodes located adjacent to each other, which belong to two different groups, to be also contacted via a feed cable of the adjacent group. It was surprisingly found that the magnetic cross-talk and hence also the interference signal can be markedly reduced during data acquisition due to such a double electrical connection of an electrode via two separate feed cables. The double electrical connection relates preferably to electrodes that are located in the boundary area of adjacent groups, and different, multiwire feed cables are present between two adjacent electrodes. The term "electrodes located adjacent to each other" is defined such that it is two adjacent electrodes that have contact with the skin surface. Should a defect electrode be present, which is not in contact with the skin and current feed or voltage measurement is not consequently possible, the adjacent electrode is the electrode that follows the defect electrode and has contact with the skin.

The method of determining measured signals with a device for electroimpedance tomography by means of an electrode belt, which has at least two groups of electrodes located next to each other, which are each contacted via multiwire feed cables, comprises the electrical connection of at least one electrode of two electrodes located adjacent to each other, which belong to different groups, with an additional electrode feed line, which extends via the feed cable of the group of electrodes located adjacent to that electrode. Additionally electrically connecting both electrodes located adjacent to each other via the feed cable of the respective adjacent group of electrodes is also within the scope of the present invention.

An exemplary embodiment of the device according to the present invention is shown in the figure and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
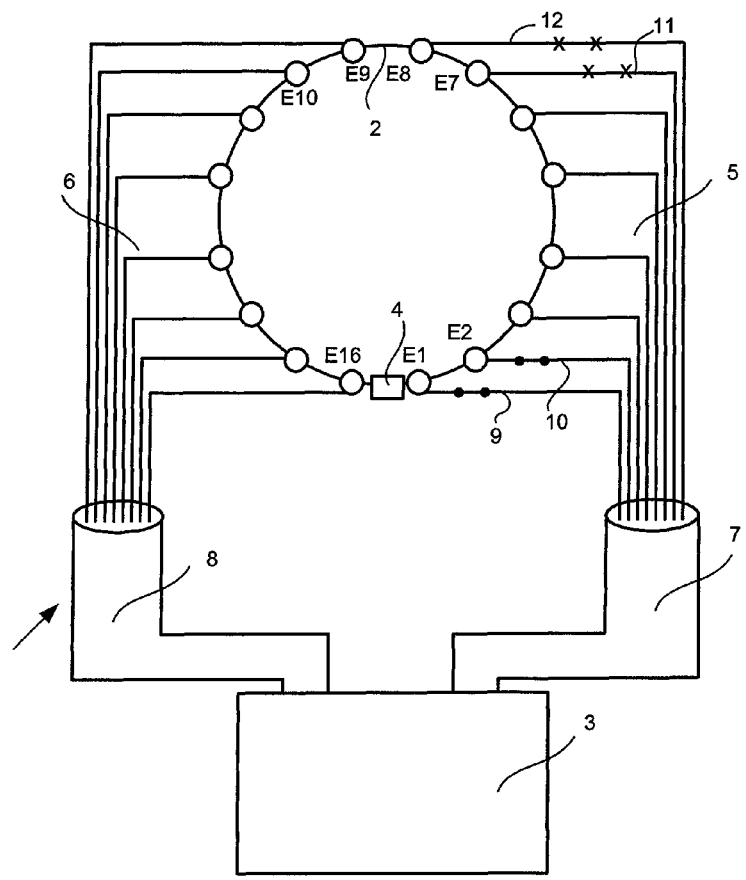
FIG. 1 is a schematic view showing a device for electroimpedance tomography with an analyzer and an electrode belt.

Referring to the drawings in particular, FIG. 1 shows a measuring device 1 for electroimpedance tomography with an electrode belt 2 and with an analyzer 3 connected to the electrode belt 2. The electrode belt 2 has a belt buckle 4, at which the electrode belt 2 can be opened, and 16 electrodes E1 through E16, which are arranged at equally spaced locations at the electrode belt 2. The electrodes are divided into a first group 5 of eight electrodes E1 through E8 located next to each other and into a second group 6 of likewise eight electrodes E9 through E16 located next to each other. The first group 5 of electrodes E1 through E8 is contacted with a first, multiwire feed cable 7, and the second group 6 of electrodes E9 through E6 is connected to a second, multiwire feed cable 8. FIG. 1 illustrates as an example a current feed via the electrode feed lines 9, 10 and the electrodes E1 and E2 and a voltage measurement via the electrode feed lines 11, 12 and the electrodes E7 and E8. All electrode feed lines (9, 10, 11, 12) for the current feed and the voltage measurement extend within the first feed cable 7 in the example being shown, so that there is only a slight cross-talk and hence a low interference signal.

Figure 2:
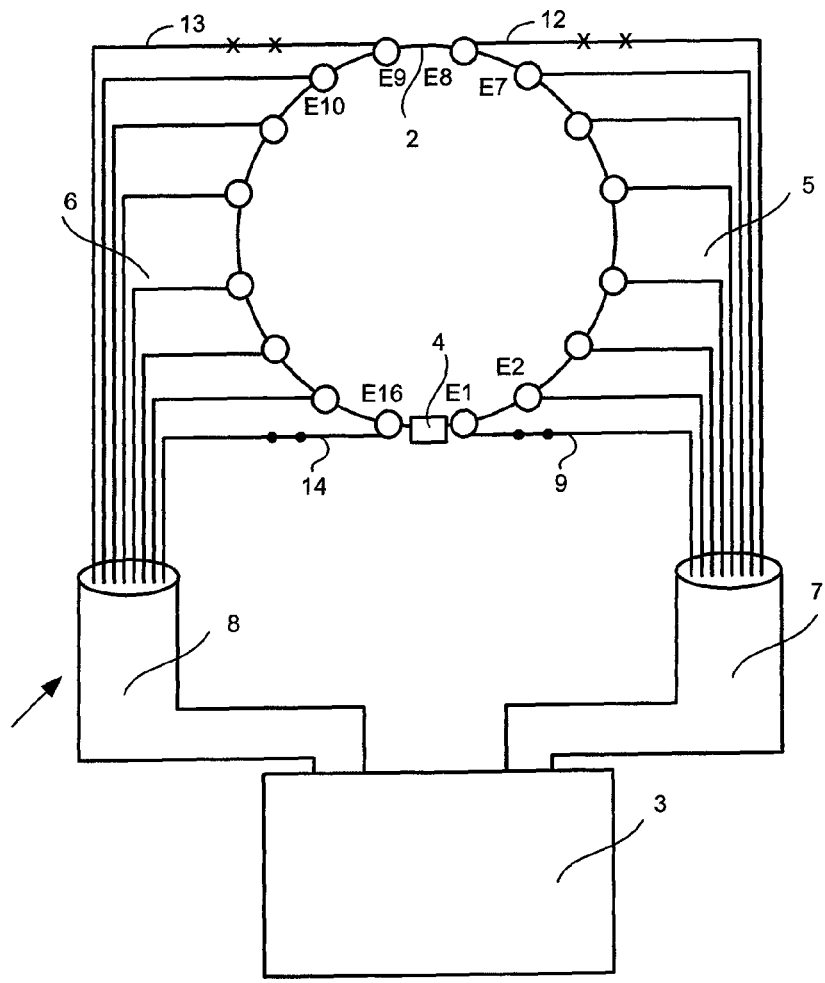
FIG. 2 is a schematic view showing an alternative operating state to FIG. 1.

FIG. 2 illustrates an alternative operating state compared to FIG. 1, in which the current feed takes place via the electrode leads 9, 14 and the electrodes E1 and E16, and the voltage measurement is performed via the electrode feed lines 12, 13 and the electrodes E8 and E9. The electrode feed lines 9, 14 for the current feed as well as the electrode feed lines 12, 13 for the voltage measurement extend in different feed cables 7, 8 here, so that there is maximum cross-talk with a high interference signal.

Figure 3:
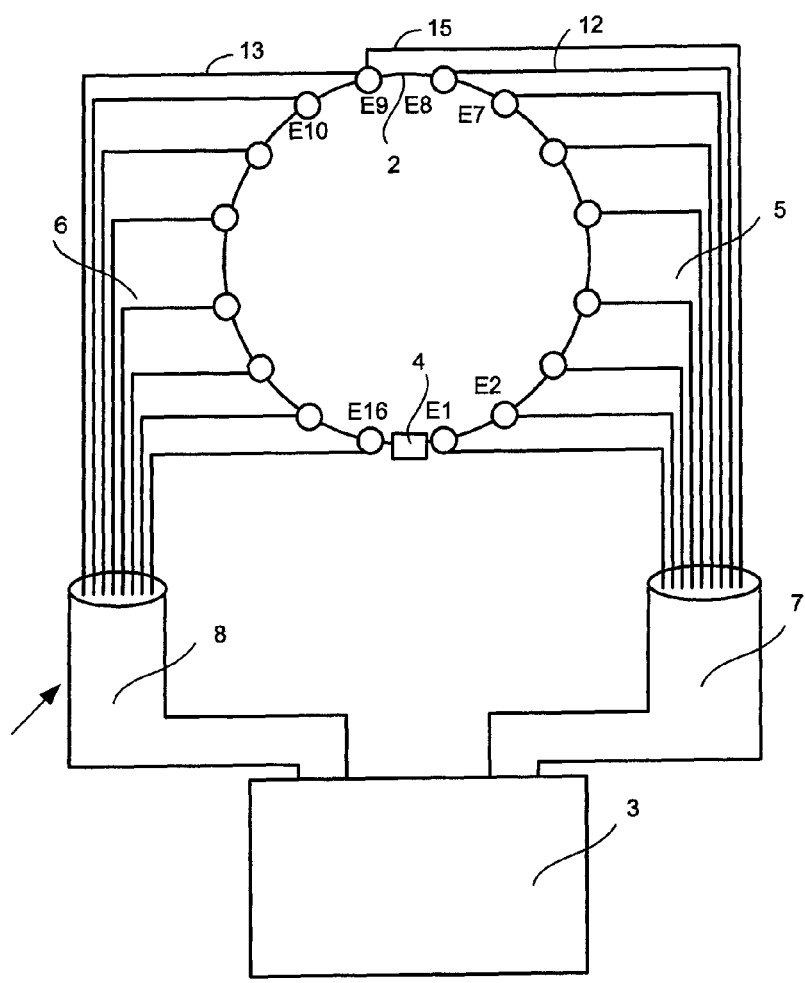
FIG. 3 is a schematic view showing an electrical connection embodiment according to the present invention.

FIG. 3 shows the electrical connection of the electrodes E9 according to the present invention, in which there additionally is an electrical connection via an electrode feed line 15 extending through the first feed cable 7 besides the electrode feed line 13 extending through the second feed cable 8. This double electrical connection pertains to one of two mutually adjacent electrodes E8 and E9 or E16 and E1 of two different groups 5, 6 of electrodes E1 through E8 and E9 through E16. As an alternative to electrode E9, the double electrical connection may also be performed via electrode E8 or via electrodes E1 or E16, or the double electrical connection is present in each of the electrode pairs E1, E16; E8, E9 located adjacent to each other, which is not shown in FIG. 3 for the sake of greater clarity.

While specific embodiments of the invention have been shown and described in detail to illustrate the application of the principles of the invention, it will be understood that the invention may be embodied otherwise without departing from such principles.

LIST OF REFERENCE NUMBERS

1 Measuring device
2 Electrode belt
3 Analyzer
4 Belt buckle
5 First group of electrodes
6 Second group of electrodes
7 First feed cable
8 Second feed cable
9-15 Electrode feed line
E1-E16 Electrodes

What is claimed is:

1. A device for electroimpedance tomography, the device comprising:

an electrode belt with electrodes comprising a first group of electrodes and a second group of electrodes, said first group of electrodes being located adjacent to said second group of electrodes, said electrodes including an adjacent pair of electrodes comprising an electrode of said first group of electrodes located adjacent to an electrode of said second group of electrodes;

a first group multiwire feed cable comprising electrode feed lines electrically connected to respective electrodes of said first group of electrodes; and a second group multiwire feed cable comprising electrode feed lines electrically connected to respective electrodes of said second group of electrodes, wherein the second group multiwire feed cable comprises an additional electrode feed line electrically connected to the electrode of said first group of electrodes of said adjacent pair of electrodes such that the electrode of said first group of electrodes of said adjacent pair of electrodes is electrically connected to an electrode feed line of said first group multiwire feed cable and also electrically connected to an electrode feed line of said second group multiwire feed cable.

2. A device in accordance with claim 1, further comprising a belt buckle at the electrode belt, wherein said two groups of electrodes are located on each of two sides of said belt buckle, and said adjacent pair of electrodes are located at a beginning of the belt on both sides of the belt buckle or at an end of the respective group.

3. A method for determining measured signals with a device for electroimpedance tomography, the method comprising the steps of:
providing an electrode belt comprising a first group of electrodes and a second group of electrodes located next to each other;
providing a first group multiwire feed cable comprising electrode feed lines;
electrically connecting the electrode feed lines of the first group multiwire feed cable to each of the respective electrodes of the first group of electrodes;
providing a second group multiwire feed cable comprising electrode feed lines;
electrically connecting the electrode feed lines of the second group multiwire feed cable to each of the respective electrodes of the second group of electrodes;
providing the second group multiwire feed cable with an additional electrode feed line;
electrically connecting the additional electrode feed with an electrode of the first group of electrodes such that the electrode of said first group of electrodes is electrically connected to an electrode feed line of said first group multiwire feed cable and also electrically connected to the additional electrode feed line of said second group multiwire feed cable.

4. A method in accordance with claim 3, further comprising providing a belt buckle at the electrode belt, wherein said two groups of electrodes are located on each of two sides of said belt buckle, and said adjacent pair of electrodes are located at a beginning of the belt on both sides of the belt buckle or at an end of the respective group.

5. A device for electroimpedance tomography, the device comprising:
an electrode belt with electrodes comprising a first group of electrodes and a second group of electrodes, said first group of electrodes being located adjacent to said second group of electrodes to provide an adjacent pair of electrodes comprising an electrode of said first group of electrodes located adjacent to an electrode of said second group of electrodes;
a first group multiwire feed cable comprising electrode feed lines with electrode feed lines of said first group multiwire feed cable electrically connected to respective electrodes of said first group of electrodes;
a second group multiwire feed cable comprising electrode feed lines with electrode feed lines of said second group multiwire feed cable electrically connected to respective electrodes of said second group of electrodes; and
an additional electrode feed line electrically connected to one of said adjacent pair of electrodes, said additional electrode feed line being part of one of said first group multiwire feed cable and said second group multiwire feed cable such that said one of said adjacent pair of electrodes is electrically connected to an electrode feed line of said first group multiwire feed cable as well as electrically connected to an electrode feed line of said second group multiwire feed cable.

6. A device in accordance with claim 5, further comprising a belt buckle at the electrode belt, wherein said two groups of electrodes are located on each of two sides of said belt buckle, and said adjacent pair of electrodes are located at a beginning of the belt on both sides of the belt buckle or at an end of the respective group.

7. A device in accordance with claim 5, further comprising another additional electrode feed line connected to another of said adjacent pair of electrodes, said another additional electrode feed line being part of one of said first group multiwire feed cable and said second group multiwire feed cable such that said another of said adjacent pair of electrodes is electrically connected to an electrode feed line of said first group multiwire feed cable as well as electrically connected to an electrode feed line of said second group multiwire feed cable.

8. A device for electroimpedance tomography, the device comprising:
an electrode belt;
a first group of electrodes connected to the electrode belt, the first group of electrodes including a two feed line electrode;
a second group of electrodes connected to the electrode belt, the second group of electrodes including a first group adjacent electrode, connected to the belt at a position adjacent to the two feed line electrode of the first group of electrodes;
a first group multiwire feed cable comprising first group electrode feed lines, each of the first group electrode feed lines being connected to a respective one of the electrodes of said first group of electrodes, whereby one of said first group electrode feed lines is electrically connected to said two feed line electrode;
a second group multiwire feed cable comprising second group electrode feed lines, each of the second group electrode feed lines being connected to a respective one of the electrodes of said second group of electrodes, whereby one of said second group electrode feed lines is electrically connected to said first group adjacent electrode, wherein said second group multiwire feed cable further comprises:
an additional electrode feed line electrically connected to said two feed line electrode, said additional electrode feed line being part of said second group multiwire feed cable, whereby said two feed line electrode is electrically connected to said additional electrode feed line of said second group multiwire feed cable and is also electrically connected to said one of said first group electrode feed lines of said first group multiwire feed cable.

\* \* \* \* \*